United States Patent [19]

Vroman

[11] Patent Number: 5,492,114
[45] Date of Patent: Feb. 20, 1996

[54] NON-REBREATHING OXYGEN MASK

[76] Inventor: Holly Vroman, 434 Devils La., Ballston Spa, N.Y. 12020

[21] Appl. No.: 293,754
[22] Filed: Aug. 22, 1994
[51] Int. Cl.⁶ .................................................. A62B 37/00
[52] U.S. Cl. .................. 128/205.13; 128/205.17; 128/205.25
[58] Field of Search ...................... 128/911, 912, 128/DIG. 26, 205.13, 205.17, 205.25

[56] References Cited

U.S. PATENT DOCUMENTS

| | | | |
|---|---|---|---|
| 3,196,866 | 6/1965 | Adams | 128/205.13 |
| 4,000,341 | 12/1976 | Matson. | |
| 4,440,163 | 4/1984 | Spergel. | |
| 4,737,153 | 4/1988 | Shimamura et al.. | |
| 5,036,890 | 8/1991 | Whaley | 138/109 |
| 5,121,746 | 6/1992 | Sikora. | |

FOREIGN PATENT DOCUMENTS 949074  7/1961  United Kingdom .............. 128/205.13

Primary Examiner—Edgar S. Burr
Assistant Examiner—Virendra Srivastava
Attorney, Agent, or Firm—Gerhard K. Adam

[57] ABSTRACT

A non-rebreathing oxygen mask for supplying a continuous flow of oxygen to a patient. The non-rebreathing oxygen mask includes a face mask portion for enclosing the mouth and nose of a patient, an oxygen reserve bag for receiving a supply of oxygen from an external source, and an intermediate oxygen entry port for regulating the flow of oxygen into the oxygen reserve bag from an external source, and between the oxygen reserve bag and the face mask portion. A spring member, having a first end portion secured to a distal end of the oxygen entry port and a second end freely extending through the neck of the oxygen reserve bag into the interior thereof, is utilized to maintain an unobstructed airflow passageway through the neck area of the oxygen reserve bag.

2 Claims, 3 Drawing Sheets 5,492,114

NON-REBREATHING OXYGEN MASK

FIELD OF THE INVENTION

The present invention relates to an oxygen mask and, more particularly, to an improved non-rebreathing oxygen mask for supplying a continuous flow of oxygen to a patient. The non-rebreathing oxygen mask of the present invention is conventional in construction and generally includes a face mask portion for enclosing the mouth and nose of a patient, an oxygen reserve bag for receiving a supply of oxygen from an external source, and an oxygen entry port, disposed intermediate the face mask portion and said oxygen reserve bag, for regulating the flow of oxygen into the oxygen reserve bag, and the flow of oxygen from the oxygen reserve bag into the face mask portion. Advantageously, a spring member, having a first end portion secured to a distal end of the oxygen entry port and a second end freely extending through the neck of the oxygen reserve bag into the interior thereof, is utilized to maintain an unobstructed airflow passageway through the neck area of the oxygen reserve bag, thereby ensuring that the patient receives an uninterrupted, potentially life-saving, supply of oxygen.

BACKGROUND OF THE INVENTION

Currently available non-rebreathing oxygen mash generally include the above-described face mask portion, oxygen reserve bag and intermediate oxygen entry port, with the oxygen reserve bag attached around, and extending away from, the distal end of the oxygen entry port. The oxygen reserve bag is typically constructed from a thin plastic material, and is configured in the shape of a bottle having a thin neck area, a wider main body, and a shoulder portion, having a gradually increasing width, joining the neck area and the main body of the oxygen reserve bag.

The face mask portion of a non-rebreathing oxygen mask is secured over the nose and mouth area of a patient using a head strap. When the face mask portion is suitably positioned, the main body of the oxygen reserve bag extends outwardly over the upper chest of the patient.

In normal operation, sufficient oxygen should be supplied to the oxygen reserve bag through the oxygen entry port to continuously inflate the oxygen reserve bag to at least two-thirds of its full volume. Unfortunately, as described in detail hereinbelow, this operational inflation requirement and the operational orientation of the oxygen reserve bag relative to a patient's chest, oftentimes result in a pinching off of the thin neck area of the oxygen reserve bag, deleteriously impeding the flow of oxygen to a patient.

SUMMARY OF THE INVENTION

In order to avoid the disadvantages of the prior art, the present invention utilizes a spring member to maintain an unobstructed airflow passageway through the neck area of the oxygen reserve bag, thereby ensuring that a patient receives an uninterrupted supply of oxygen. Specifically, the spring member includes a first end portion secured to a distal end of the oxygen entry port and a second end portion extending freely through the neck area and into the interior of the oxygen reserve bag. Accordingly, even if the neck area is crushed or otherwise impeded, the spring member will ensure that an adequate supply of oxygen will flow from the oxygen reserve bag to the attached face mask portion.

BRIEF DESCRIPTION OF THE DRAWINGS

These and other features of the present invention will become readily apparent upon reading the following detailed description and upon reference to the drawings in which.

DETAILED DESCRIPTION OF THE INVENTION

Figure 1:
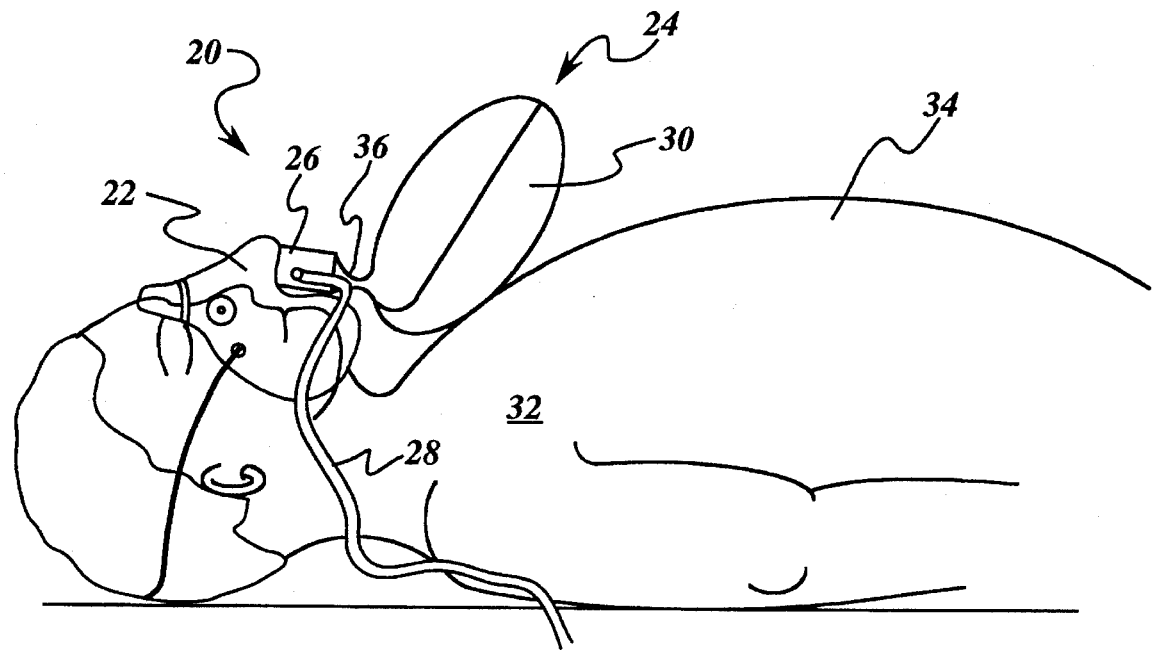
FIG. 1 illustrates the non-rebreathing oxygen mask of the prior art with the neck area of the oxygen reserve bag pinched off, thereby impeding not only the flow of oxygen from an external source into the oxygen reserve bag, but also the flow of oxygen from the oxygen reserve bag into the face mask portion.

Referring now specifically to the drawings, there is illustrated an improved non-rebreathing oxygen mask, generally designated as 10, in accordance with a preferred embodiment of the present invention, wherein like reference numerals refer to like components throughout the drawings.

A conventional non-rebreathing oxygen mask 20 is illustrated in FIG. 1. The non-rebreathing oxygen mask 20 includes a face mask portion 22, an inflatable oxygen reserve bag 24 and an oxygen entry port 26 for regulating the flow of oxygen into the oxygen reserve bag 24, and the flow of oxygen between the oxygen reserve bag and the face mask portion 22. Oxygen is supplied to the oxygen entry port 26 from a pressurized oxygen supply (not shown) through an oxygen supply tube 28. A one-way valve 29 (FIG. 2), disposed on the end of the oxygen entry port 26 proximate the face mask portion 22, controls the direction of oxygen flow through the non-rebreathing oxygen mask 20; oxygen is only allowed to flow into the face mask portion 22.

As shown in FIG. 1, the oxygen reserve bag 24 is designed to be continuously inflated to at least two-thirds of its full operational volume. The flow of oxygen through the oxygen supply tube 28 is carefully controlled, depending upon the requirements of a particular patient, to maintain at least the minimum required operational volume.

When the oxygen reserve bag 24 is properly inflated, the main body 30 of the bag 24 typically rests on the upper chest area 32 of the patient 34, and is bent away from the longitudinal axis of the oxygen entry port 26. Unfortunately, the obtuse relative orientation of the main body 30 of the oxygen reserve bag 24 and the oxygen entry port 26 oftentimes results in the deleterious pinching-off of the neck area 36 of the bag 24, potentially reducing the flow of oxygen into the face mask portion 22. Since the non-rebreathing oxygen masks of the prior art generally have no provision for the entrainment of room air should the flow of oxygen from the oxygen reserve bag cease, the patient may be deprived of a sufficient supply of oxygen.

Figure 2:
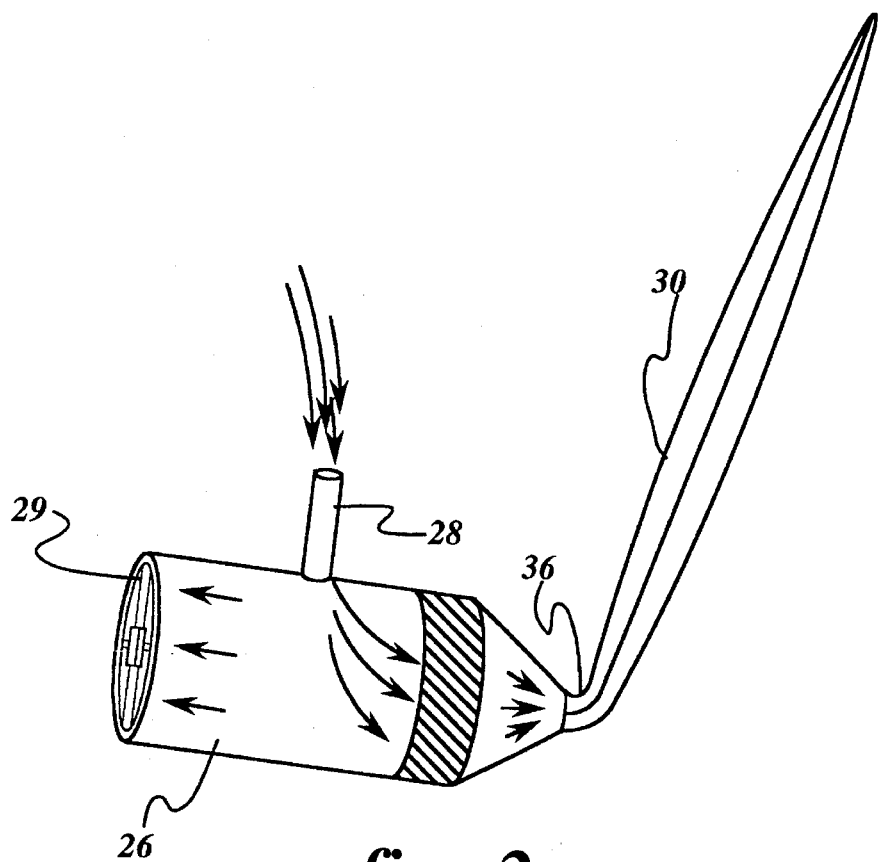
FIG. 2 is a partial enlarged view of the non-rebreathing oxygen mask of FIG. 1, illustrating the impeded oxygen flow through the oxygen entry port and the pinched-off neck area of the oxygen reserve bag.

The pinching-off of the neck area 36 of the oxygen reserve bag, and the resultant oxygen flow restrictions originating therefrom, are shown in detail in FIG. 2. Specifically, the pinching-off of the neck area 36 impedes not only the supply of oxygen flowing into the face mask portion 22 from the oxygen reserve bag 24, but also the external supply of oxygen flowing through the oxygen supply tube 28 and oxygen entry port 26 into the oxygen reserve bag 24.

Figure 3:
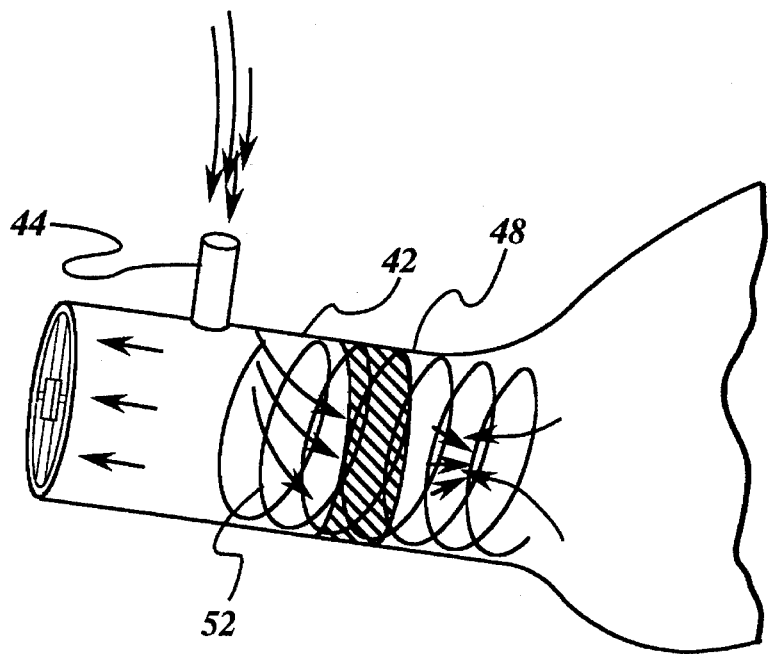
FIG. 3 is a partial enlarged view of a non-rebreathing oxygen mask in accordance with a preferred embodiment of the present invention, with a spring member having a first end secured to the oxygen entry port and a second end extending through the neck area of the oxygen reserve bag into the interior thereof.
Figure 4:
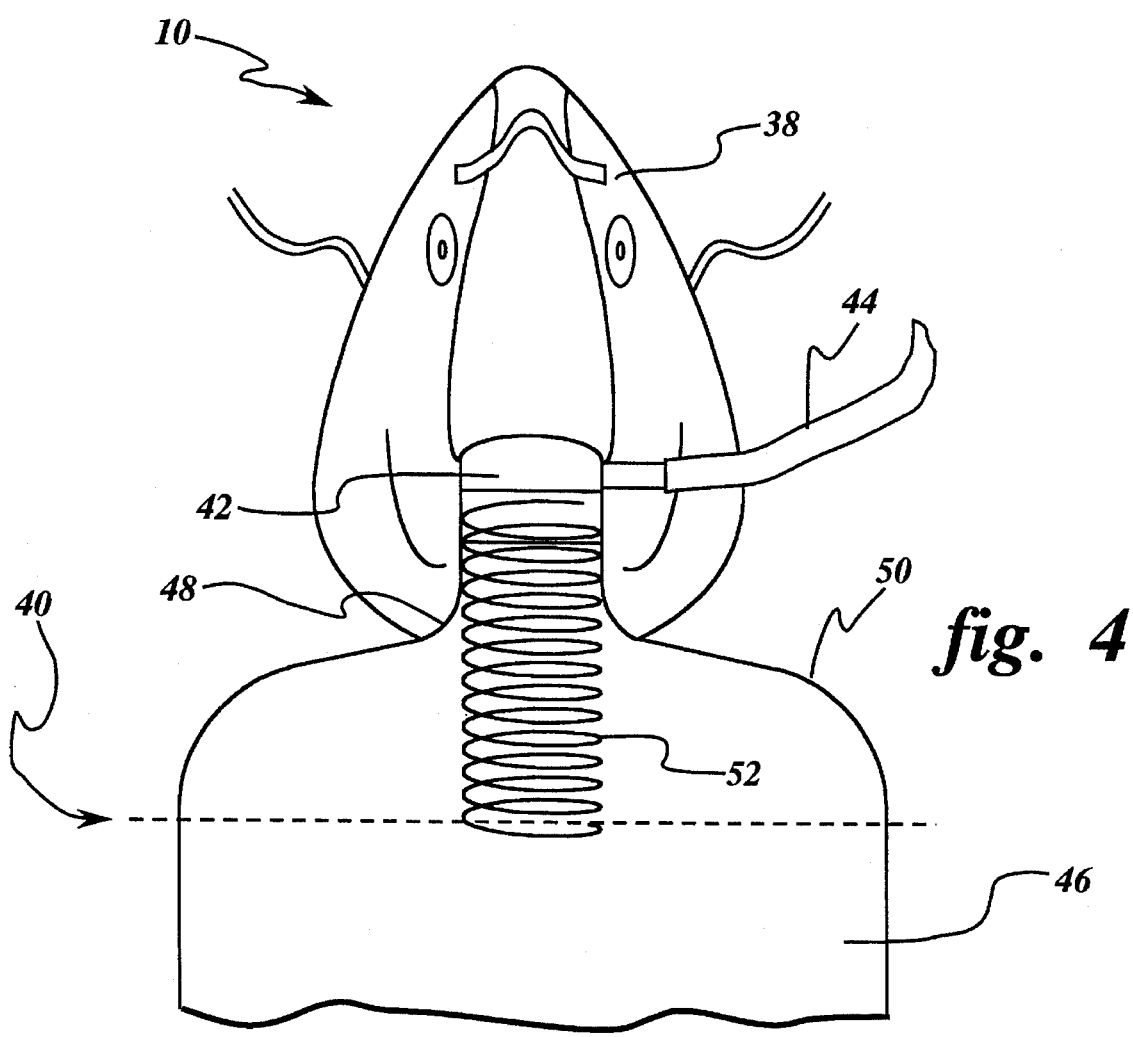
FIG. 4 illustrates a non-rebreathing oxygen mask in accordance with a preferred embodiment of the present invention.

Referring now specifically to FIGS. 3 and 4, there is illustrated an improved non-rebreathing oxygen mask 10 in accordance with a preferred embodiment of the present invention. The non-rebreathing oxygen mask 10 includes a face mask portion 38, an inflatable oxygen reserve bag 40 and an oxygen entry port 42 for regulating the flow of oxygen between the oxygen reserve bag 40, the face mask portion 38 and an oxygen supply tube 44. Again, the oxygen reserve bag 40 comprises a main body 46, a neck area 48 and a shoulder portion 50, having a gradually increasing width, joining the neck area 48 and the main body 46 of the oxygen reserve bag 40.

Figure 5:
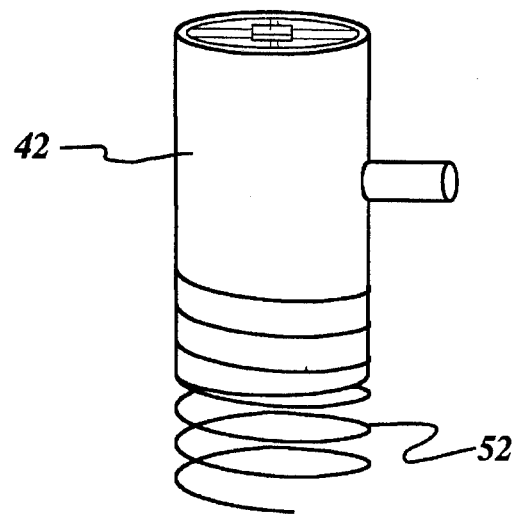
FIG. 5 illustrates the threaded attachment of the spring member to the oxygen entry port.

To prevent the potentially hazardous pinching-off of the neck area 48 of the oxygen reserve bag 40, a spring member 52, formed of plastic, metal or any other suitable material, is inserted into the neck area 48. A first end portion of the spring member 52 is secured to a distal end of the oxygen entry port 42. Preferably, the first end portion of the spring member 52 is threadedly fastened about the distal end of the oxygen entry port 42 as illustrated in FIG. 5. Of course, other securing methods may be employed to fasten the spring member 52 to the oxygen entry port 42. The spring member 52 is formed independently of said oxygen reserve bag 40.

Figure 6:
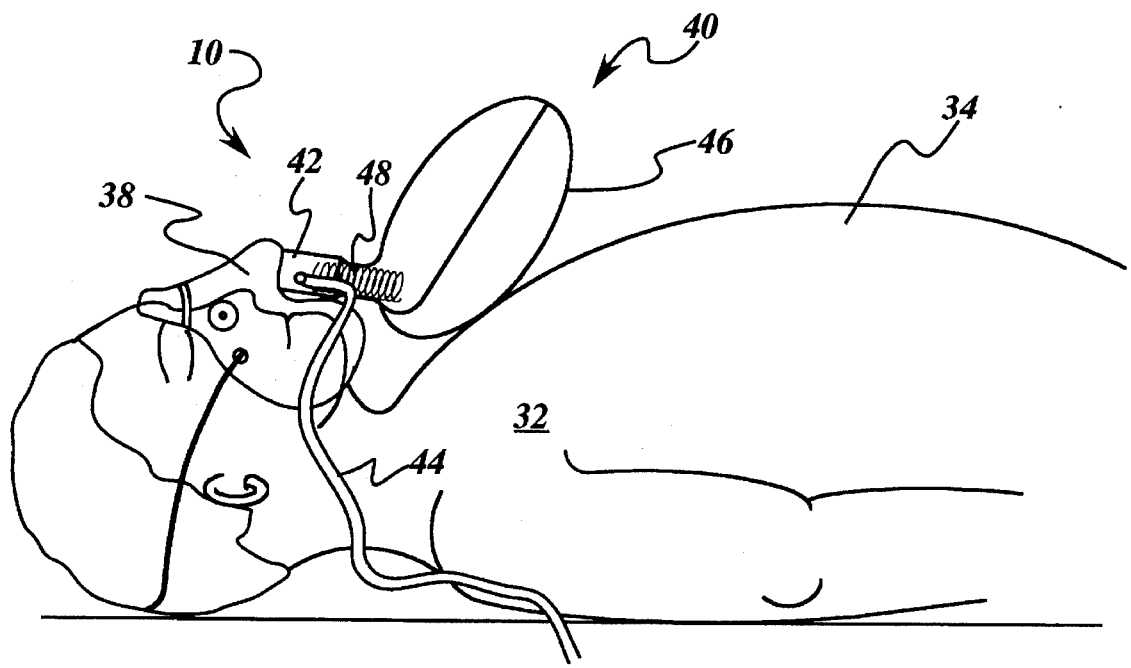
FIG. 6 illustrates the operation of the improved non-rebreathing oxygen mask of the present invention.

A second end portion of the spring member 52 freely extends through the neck area 48 of the oxygen reserve bag 40, past the shoulder portion 50 thereof, and protrudes into the main body 46 of the bag (FIGS. 3–5). Accordingly, the length of the spring member 52 is dependent upon the overall combined length of the neck area 48 and shoulder portion 50 of the oxygen reserve bag 40. By extending the second end portion of the spring member 52 past the shoulder portion 50, an open channel is maintained between the oxygen entry port 42 and the oxygen reserve bag 40, even if the neck area 48 is crushed, bent and/or flattened. In accordance with the present invention, the spring member 52 should be robust enough to prevent the complete closure of the neck area 48 of the oxygen reserve bag. Comparing FIGS. 1 and 6, it should be readily apparent that the spring member 52 prevents the pinching-off of the neck area 48 of the oxygen reserve bag when the main body 46 of the bag 40 is bent away from the longitudinal axis of the oxygen entry port 42 by the upper chest of a patient.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

I claim:

1. An improved oxygen mask of the type having a face mask for enclosing the nose and mouth of a person, an inflatable oxygen reserve bag comprising a main body and a neck portion, said inflatable oxygen reserve bag being constructed from a thin plastic material and further including a shoulder portion, said shoulder portion extending between said neck portion and said main body, and a means for providing the flow of oxygen into the face mask and the oxygen reserve bag and including an oxygen entry port, said improvement comprising a means for maintaining an unobstructed flow passageway through the neck portion of the oxygen reserve bag, said means for maintaining the unobstructed flow comprising a helical flexible member having spaced mutually adjacent coils and having one end portion of said flexible member secured near a distal end of said oxygen entry port and having a second end portion freely extending into the main body of said oxygen reserve bag through the neck portion and the shoulder portion of said oxygen reserve bag into the interior thereof for a sufficient distance to provide a suitable means for allowing movement of said oxygen reserve bag and to prevent obstructing the passageway.

2. The oxygen mask according to claim 1, wherein said one end portion of said flexible member is threadedly secured to the distal end of said oxygen entry port.

* * * * *